United States Patent [19]

Morgan

[11] Patent Number: 4,827,016

[45] Date of Patent: May 2, 1989

[54] METHOD AND COMPOUNDS FOR REDUCING DERMAL INFLAMMATIONS

[76] Inventor: Lee R. Morgan, 725 Topaz St., New Orleans, La. 70124

[21] Appl. No.: 75,579

[22] Filed: Jul. 20, 1987

Related U.S. Application Data

[63] Continuation-in-part of Ser. No. 776,579, Sep. 16, 1985, and Ser. No. 776,580, Sep. 16, 1985.

[51] Int. Cl.$^4$ .................. C07C 149/43; C07C 149/41
[52] U.S. Cl. ........................................ 560/16; 562/426; 564/154; 564/163; 564/170; 568/75
[58] Field of Search ............... 514/562, 563, 542, 620, 514/617; 564/154, 159, 201, 215, 163, 170; 568/22, 75; 560/16; 562/426

[56] References Cited

U.S. PATENT DOCUMENTS

| | | | |
|---|---|---|---|
| 3,091,569 | 5/1963 | Sheffner | 514/562 |
| 4,154,946 | 5/1979 | Ondetti et al. | 560/16 |
| 4,176,197 | 11/1979 | Olson | 514/562 |
| 4,331,648 | 5/1982 | Myers, Jr. et al. | 514/34 |
| 4,440,788 | 4/1984 | Terayama et al. | 564/154 |
| 4,526,999 | 7/1985 | Durette et al. | 564/163 |
| 4,571,430 | 2/1986 | Byrne et al. | 562/426 |
| 4,708,965 | 11/1987 | Morgan | 514/563 |
| 4,721,705 | 1/1988 | Schreuder | 514/562 |
| 4,724,239 | 2/1988 | Morgan | 514/563 |

*Primary Examiner*—Paul Lieberman
*Assistant Examiner*—Helene Kirschner
*Attorney, Agent, or Firm*—Klarquist, Sparkman, Campbell, Leigh & Whinston

[57] ABSTRACT

Dermal inflammations which are induced and propagated by leukotrienes are treated by topically applying to the inflamed dermis the following compound:

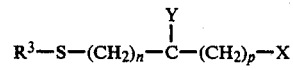

wherein $R^3$ is H or a thiol; n is 1 to 12; p is 0 to 12; X is a substituted carbonyl, such as an ester or a carboxylic acid; and Y is an aliphatic or branched hydrocarbon, aromatic ring, carbonyl or substituted amide.

12 Claims, No Drawings

METHOD AND COMPOUNDS FOR REDUCING DERMAL INFLAMMATIONS

CROSS REFERENCE TO RELATED APPLICATIONS

This application is a continuation-in-part of copending U.S. patent applications Ser. Nos. 06/776,579, filed Sept. 16, 1985, and 06/776,580 filed Sept. 16, 1985, the disclosures of which are incorporated by reference.

BACKGROUND OF THE INVENTION

1. Field of the Invention

This invention relates to the treatment of indolent dermal irritations. More specifically, it concerns treatment of persistent inflammations such as chemical ulcers, herpes ulcers, radiation burns, psoriasis and sunburn.

2. General Background of the Invention

Herpes ulcers, radiation burns, psoriasis and some chemical ulcers are indolent inflammations for which medical treatment has been unavailable or inadequate. Each of these conditions produces dermal eruptions and ulcers which persist painfully, sometimes for many months.

Herpes Infections

Infections caused by the herpes simplex virus produce eruptions of one or more groups of vesicles or sores on the human body. Such eruptions characteristically occur on the vermillion border of the lips, at the external nares, on the glans, prepuce or vulva.

Herpes simplex virus type 1 is known as the "skin" or "above the umbilicus" virus and type 2 is known as the "genital" or "below the umbilicus" virus. The types cannot be distinguished in a culture, but can be distinguished on the basis of antibodies generated upon exposure to the virus. The two types cross react with one another in the laboratory and are, thus, very closely related to each other.

Herpes infections are commonly recrudescent and reappear during other febrile illness or even physiological states such as menstruation and high stress.

Some herpes lesions, particulary those produced by herpes zoster, develop eruptive lesions in a linear pattern along dermal distributions of nerves on the face, trunk, abdomen, and extremities to produce extremely painful, eruptive, weeping lesions that heal extremely slowly with paraphia. This type of infection is known as shingles and is seen in individuals with cancer or opportunistic debilitating infections that depress the immune system of the patient.

Various treatments for herpes hominis simplex have been proposed. Asculai, U.S. Pat. No. 4,147,803, reports that certain sorbitan derivatives have antiherpetic activity. DeLong et al. (U.S. Pat. No. 3,639,612) describes such activity for certain chalcogen containing heterocyclic compounds. Stedman (U.S. Pat. No. 3,555,355) discloses that certain cycloalkylamines have activity against herpes simplex as does cycloheximide (U.S. Pat. No. 4,427,684). Fleming et al. (U.S. Pat. No. 3,829,578) teaches that certain bis-basic ethers and xanthen-9-ones have anti-viral activity and Soichet (U.S. Pat. No. 4,312,884) describes such antiviral activity by Spectinomycin.

Kaufman et al., (*Arch. Ophthalmol.*, 68:235-239 (1962)) reported treatment of herpes simplex keratitis with 5-iodo-2-deoxyuridine (IUD). Schabel describes treatment of genital herpetic infection with 9-beta-D-arabino-fluranosyl adenine (*Chemotherapy*, 13:321-338 (1968)), and reported antiviral activity of 5-trifluoromethyl-2-deoxyuridine (*N.Y. Acad. Sci.*, 130:168-180 (1965)). Adams et al. (*J. Infect. Dis.*, 133 (suppl) 151-159 (1976)) treated genital herpes infections with topical application of adenine arabinoside. Felber et al. (*JAMA*, 223:289-292 (1973)) describes treatment of herpes infections by application of a vital dye as neutral red or proflavine followed by exposure to light. Cheseman et al. (*N. Eng. J. Med.*, 300:1345-1349 (1979)) and Pazin et al. (*N. Engl. J. Med.*, 301:225-230 (1979)) report the treatment of herpes simplex infection by human leukocyte interferon. Blough and Giuntoli (*JAMA*, 241:2798-2801 (1979)) described treatment of human genital herpes infections with 2-deoxy-D-glucose. Schaeffer et al. (*Nature*, 272:583-585 (1978)), Fyfe et al. (*J. Biol. Chem.*, 253:8721-8727 (1978)), Sely et al. (*Lancet*, 2:1257-1270 (1979)), Park et al. (*J. Infect. Dis.*, 140:802-806 (1979)), and Pavan-Langston et al. (*Am. J. Ophthalmol.*, 86:618-623 (1978)) reported treatment of herpes infections by 9-(2-hydroxyethoxymethyl) guanine (Acyclovir). Fisher (*Cutis*, 29:467-472 (1982)) described treatment of herpes simplex infections with Amantadine Hydrochloride.

Other forms of treatment of herpes hominis simplex Type I and II include a variety of agents such as lysine, ascorbic acid, topical ether and topical chloroform, thymol, nonionic surfactants (U.S. Pat. Nos. 4,147,803 and 4,185,097) inactivated herpes viruses, zinc, urea, tannic acid (U.S. Pat. No. 4,285,934), glutaraldehyde, cow pox vaccine, intradermal injections of gamma globulins, and a surgical treatment by epidermal excisions of the herpetic lesions.

A mixture of L-lysine, gibberellic acid and urea has been reported to be useful in the treatment of H. simplex (U.S. Pat. No. 4,424,232). Similarly, transfer factor has been reported to be useful (U.S. Pat. No. 4,435,384). Adenosine monophosphate has also been reported to reduce pain and increase healing of herpes zoster lesions (JAMA).

Chemical Ulcers

Another persistent, painful type of dermal inflammation is caused by accidental soft tissue extravasations from intravenous administration of anthracyclines such as doxorubicin (DOX).

The anthracyclines have the general formula:

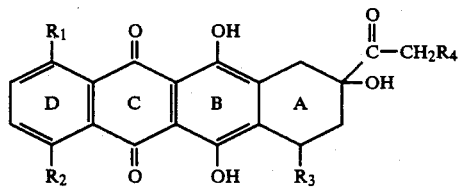

and their essential structure is based on the anthraquinone ring which characteristically has a quinone functionality on the C ring and a hydroquinone function on the B ring. In addition, a hexose sugar is commonly attached through a glycosidic linkage at $R^3$. Daunosamine is the most common sugar to be found at $R^3$, $R^1$, and $R^2$, while $R^4$ can vary widely. The two anthracyclines presently in clinical use are doxorubicin (marketed by Adria Laboratories of Dublin, Ohio as ADRIAMYCIN) and duanomycin. In doxorubicin, $R^1$, $R^2$, and $R^4$ are H, $OCH_3$, and OH; this structure is shown below:

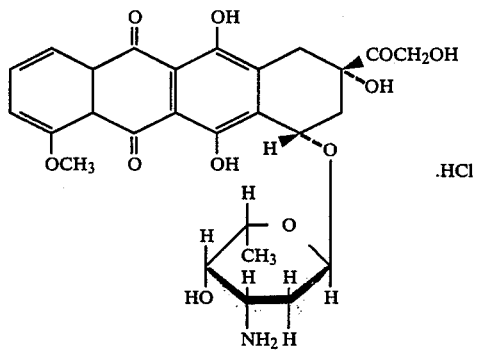

For daunomycin, $R^1$, $R^2$ and $R^4$ are H, $OCH_3$ and H, respectively, while $R^3$ is daunosamine.

The anthracyclines are members of the Rhodomycin group of antibiotics produced by Streptomyces, they have considerable activity against a wide range of human and animal tumors. Two members of this group, daunomycin and doxorubicin (DOX), are widely used as anticancer agents. However, the clinical usefulness of these drugs is impaired because they cause cardiac damage in both man and animals when administered systemically.

Another serious toxicity associated with these agents is tissue necrosis caused by extravasation into subcutaneous tissue during intravenous administration. This problem is very harmful and painful because chemical ulcers induced by anthracyclines tend to last many months and usually require surgical debridement before subsiding.

A number of agents have been injected or topically applied to treat doxorubicin (DOX) skin necrosis. Sodium bicarbonate (*Lancet,* 2:417 (1978)), alpha tocopherol, beta adrenergics, diphenhydramine and cimetidine (*Cancer Treat Res.,* 65:1001 (1981)), DMSO (*Cancer Treat. Rep.,* 67:407 (1983)) and corticosteroids (*Am. J. Nurs.,* 79:94 (1979)) have all been used, but none of them have been widely accepted.

N-acetylcysteine is an agent that has been extensively evaluated for all types of DOX toxicities. Previous reports have indicated, however, that DOX ulcers became worse when NAC was injected intradermally proximal to the ulcers in mice. (*Cancer Treat. Rep.,* 65:1001 (1981)). With the exception of corticosteroids, surgical debridement and graft placement, no satisfactory parenteral or topical formulation has been available for treating anthracycline induced ulcers.

Other Indolent Inflammations

Radiation burns and psoriasis are similar to herpes ulcers and DOX burns in that they are persistent, painful dermal inflammations that have not been very successfully treated by existing medical techniques.

Common Mechanism of Action

The present inventor has discovered that such persistent, apparently unrelated dermal inflammations as herpes ulcers, chemical burns, radiation burns and psoriasis are induced and/or propagated by leukotriene inflammatory mediators. The indolent inflammatory process results when tissue membrane destruction releases arachidonic acid, which in turn produce prostaglandins and leukotrienes as well as other inflammatory components. The leukotrienes (LTs) are mediators of ischemia, arterial constriction, neutrophil exocytosis into the dermis and epidermis, and epithelial destruction.

Leukotrienes are members of the eicosanoid family, and are the major biologically active eicosanoids of the lipoxygenase pathway of arachidonic acid metabolism. This pathway is illustrated schematically below:

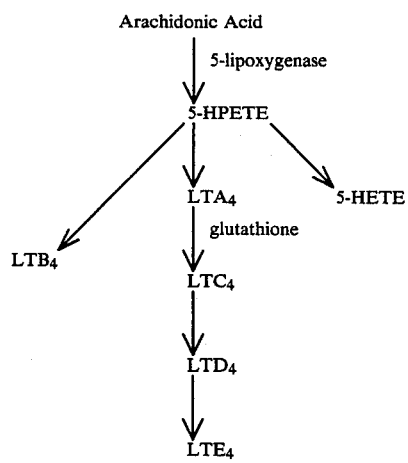

Production of the leukotrienes requires the initial interaction of arachidonic acid with a cytosolic enzyme called 5-lipoxygenase. The unstable product of this reaction is a 5-hydroperoxy-6,8,11,14-eicosatetraenoic acid (5-HPETE). The 5-HPETE is subsequently reduced to corresponding 5-hydroxy acid (5-HETE) or it may form a 5,6-epoxide intermediate referred to as leukotriene $A_4$ ($LTA_4$). $LTA_4$ is an unstable intermediate in the formation of the remaining leukotrienes. $LTA_4$ is the precursor of $LTB_4$, a potent chemotactic agent, and $LTC_4$, $LTD_4$, and $LTE_4$, which are the slow-reacting substances of anaphylaxis.

LTs are produced by a host of cell types including the pulmonary parenchymal cells, macrophage, mast cells, leukocytes, connective tissue cells, and several types of smooth muscle cells, particularly vascular smooth muscle cells. When tissue and cellular membranes are destroyed by chemical, or some other foreign irritation, arachidonic acid is released which, in the presence of lipoxygenase, initiates the above cascade to the leukotrienes and other chemical mediators of inflammation.

LTs exert a variety of biological actions that contribute to their role as mediators of ischemia and shock. $LTB_4$ plays a key role as a mediator of inflammation by virtue of its chemotactic and chemokinetic properties on blood cells (e.g. eosinophils, macrophages). $LTB_4$ also promotes the release of lysosomal hydrolases from these and other cell types accompanied by an enhancement of microvascular permeability.

In contrast to $LTB_4$, the $LTC_4$, $LTD_4$, and $LTE_4$ are more active as stimulators of smooth muscle contraction. $LTC_4$ and $LTD_4$ are long acting substances of inflammation that also produce anaphylactic reactions to toxicity and drugs. $LTC_4$ is metabolized to $LTD_4$ and then to $LTE_4$ and there is a significant loss of biological activity as metabolism progresses. Although $LTC_4$ and $LTD_4$ are comparable to each other in activity, they are both much more active than $LTE_4$ in most biological systems.

LTB$_4$, LTC$_4$ and LTD$_4$ are therefore mediators of inflammation. As long as these agents are produced, for example, by continuous exposure to chemicals or virus-induced epithelial destruction, the above LTs and other inflammatory factors will be produced. The present inventor has established that there are elevated concentrations of tissue leukotrienes A$_4$ (LTA$_4$), C$_4$ (LTC$_4$) and D$_4$ (LTD$_4$) associated with herpes vesicles, anthracycline ulcers, radiation burns, sunburns, and psoriasis.

Some dermal inflammatons, such as thermal burns, are primarily induced and propagated by prostaglandins. This mechanism occurs when arachadonic acid is released in tissues having enzymes which metabolize the free arachadonic acid to prostaglandins and thromboxanes via the cyclooxygenase pathway. Prostaglandin induced inflammations are less indolent than those induced by leukotrienes and respond to analgesics such as acetyl salicylic acid and other nonsteroidal anti-inflammatory drugs (NSAIDS).

In contrast, tissue damage in herpes ulcers initiated by viruses can induce leukotriene release, with propagation of the inflammation by the continued presence of inflammatory mediators. In DOX induced ulcers, tissue damage results in leukotriene release and is propagated by the continued presence of any DOX and the long acting leukotrienes. Herpes ulcers and DOX ulcers are primarily induced and/or propagated by leukotrienes, as are radiation burns, sunburn and psoriasis.

Many dermal inflammations may be propagated both by leukotrienes and prostaglandins, but one or the other mechanism usually predominates. Inflammations, such as thermal contact burns, which are primarily associated with prostaglandins, are not indolent and their inflammation is substantially reduced by administering acetyl salicylic acid and/or other NSAIDS. Inflammations primarily induced and/or propagated by leukotrienes, however, are indolent. Inflammations due to leukotrienes may often persist up to many months or even years and are not substantially reduced by salicylic acid and/or NSAIDS. Primarily leukotriene mediated inflammations are often made worse by acetyl salicylic acid and/or the NSAIDS.

SUMMARY OF THE INVENTION

The present invention includes a method and compounds for treating dermal inflammations, such as those which are primarily propagated by leukotrienes. The compounds are also useful in treating prostaglandin propagated inflammations. The inflammations are treated by applying to the inflamed dermis an anti-inflammatory effective amount of the compound

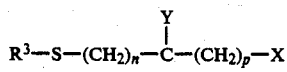

wherein R$^3$ is H or a thiol; n is 1 to 12; p is 0 to 12; X is a substituted carbonyl, such as an ester or a carboxylic acid; and Y is an aliphatic or branched hydrocarbon, aromatic ring, carbonyl or substituted amide.

Carbonyl X is preferably a carboxylic acid or an ester, such as ethyl ester.

Y is preferably a substituted amide, more preferably

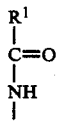

wherein most preferably R$^1$ is CH or an ultraviolet light absorbing group such as

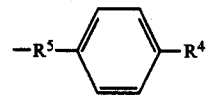

and R$^4$ or R$^5$ is an electron donating group, for example substituted or unsubstituted amine at R$^4$ or alkenyl at R$^5$.

R$^1$ is most preferably

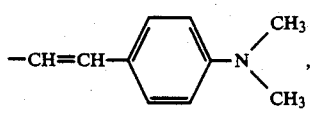

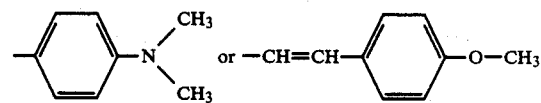

n is most preferably 1 to 4, and p is preferably 1 to 4, most preferably 1.

The present invention includes all the foregoing substituents and values for R$^1$, R$^3$, R$^4$, R$^5$, X, Y, n, and p, both alone and in any combination thereof. Also included are medicinal compositions comprising the compounds and a pharmaceutically inert carrier, such as water or DMSO. The invention also includes the compounds or compositions for use as medicaments for treating inflammations, especially dermal inflammations, such as those which are primarily induced and/or propagated by leukotrienes. Also included is use of any such composition of matter for manufacture of a medicament for therapeutic application.

The compounds and compositions are useful in treating such leukotriene propagated dermal inflammations as herpes simplex and herpes zoster ulcers, doxorubicin burns, radiation burns, and psoriasis. Inflammation in each of these conditions can be substantially reduced and caused to subside by topically dermally applying the compound to the inflammation. In some leukotriene induced inflammations, the compounds interact with peroxides and leukotriene A$_4$ (LTA$_4$) to reduce toxic free radicals and interrupt the leukotriene cascade to the highly inflammatory slow releasing substances of anaphylaxis (SRS)-LTC$_4$ and LTD$_4$. There is some evidence that the leukotriene cascade is interrupted when the compound forms an adduct with LTA$_4$. In other instances, the compounds reduce the 5-HPETE to 5-HETE, which also reduces leukotriene formation.

Prostaglandin type inflammations also have a pathway of production in which a peroxide is an intermediate. The compounds of the present invention can also react with the peroxide intermediate to interfere with prostaglandin production and decrease inflammation.

The foregoing and other objects, features, and advantages of the invention will become more apparent from the following detailed description of several preferred embodiments.

DETAILED DESCRIPTION OF PREFERRED EMBODIMENTS

The present invention became possible after the inventor determined that some indolent dermal inflammations, such as herpes ulcers, DOX burns, radiation burns and psoriasis, are primarily induced and propagated by leukotriene release in the affected tissue. Inflammation of the ulcer can be reduced or eliminated, however, by topically dermally applying compounds to the inflammation which can form an adduct with $LTA_4$, which is a highly reactive 5,6-epoxide or reduce the latter to 5-HETE. The $LTA_4$ adduct and formation of 5-HETE prevent production of $LTB_4$, $LTD_4$ and $LTE_4$ in the tissue. In the absence of these long acting mediators of inflammation, healing occurs.

The adduct forming compounds are

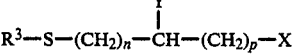

wherein $R^3$ is H or a thiol; n is 1-12; p is 0-12; X is a substituted carbonyl; and Y is an aliphatic or branched hydrocarbon, aromatic, carbonyl, or a sustituted amide.

Some of the compounds of the present invention which form adducts with the $LTA_4$ epoxide are

EXAMPLE 1

N,N'-dicetylcystine (N-DAC):

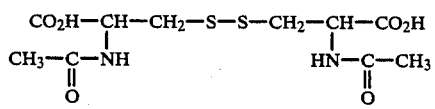

EXAMPLE 2

N-acetylhomocysteine (NAH):

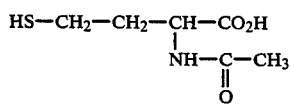

EXAMPLE 3

N-acetylcysteine (NAC):

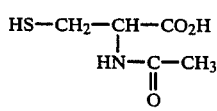

The $LTA_4$-NAC adduct which is obtained when NAC is topically applied to leukotriene propagated inflammations is shown below.

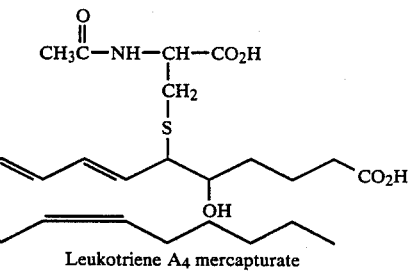

Leukotriene $A_4$ mercapturate

The thiol group of NAC binds to $LTA_4$ where indicated above. This is the same position at which the thiol group of each of the compounds of the present invention binds to $LTA_4$.

EXAMPLE 4

N-acetylcysteine ethyl ester (NACE):

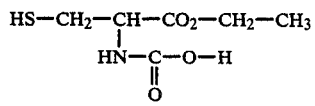

The compounds in Examples 1-4 are derivatives of the amino acids cysteine and cystine. They are preferably contained in a pharmaceutically inert carrier such as water or DMSO. On a weight basis, 5-20% N-DAC, NAC, NAH, or NACE is preferably mixed with the carrier. Although a 5-20% concentration is preferred, a concentration as high as 100% can be used. A preservative such as EDTA 0.1% may also be included. These agents effectively reduce pain and increase healing of skin vesicles, ulcers, and eruptions from herpes simplex, herpes zoster, DOX burns, radiation burns, and sunburns.

EXAMPLE 5

Another group of adduct forming compounds are especially useful in treating sunburn. These compounds are

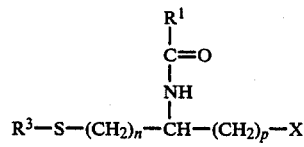

wherein $R^3$ is H or thiol; n is 1-12; p is 0-12; X is a substituted carbonyl; and $R^1$ is an ultraviolet light absorbing group such as

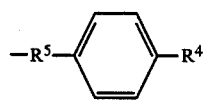

wherein $R^4$ or $R^5$ is an electron donating group. For example, $R^4$ can be a substituted amine or $R^5$ can be alkenyl.

The ultraviolet light absorbing group helps the compound act as a sunscreen while leukotriene production is also interrupted by formation of the adduct. The compound is preferably placed in an inert carrier such as peanut oil or a fragrant oil for appliction to sunburned skin. Additional sunburn damage is therefore prevented or diminished while healing takes place.

Specific examples of ultraviolet light absorbing compounds are given in subsequent Examples 6-8.

EXAMPLE 6

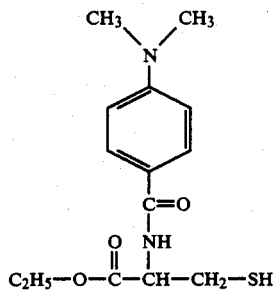

EXAMPLE 7

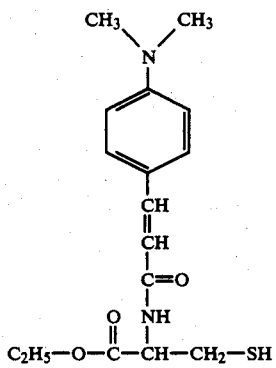

EXAMPLE 8

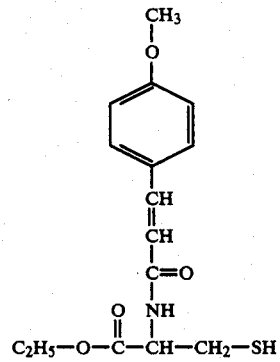

Additional examples of compounds within the scope of the invention are given in the following chart:

EXAMPLES 9-15

$$R^3-S-(CH_2)_n-\overset{Y}{\underset{|}{CH}}-(CH_2)_p-X$$

| Example No. | X | Y | n | p | $R^1$ | $R^3$ |
|---|---|---|---|---|---|---|
| 9 | COOH | NHCOR$^1$ | 3 | 1 | CH$_3$ | H |
| 10 | COOCH$_3$ | NHCOR$^1$ | 4 | 2 | CH$_3$ | H |
| 11 | COOCH$_3$ | NHCOR$^1$ | 12 | 4 | CH$_3$ | H |

-continued $$R^3-S-(CH_2)_n-\overset{Y}{\underset{|}{CH}}-(CH_2)_p-X$$

| Example No. | X | Y | n | p | $R^1$ | $R^3$ |
|---|---|---|---|---|---|---|
| 12 | COOH | C$_2$H$_5$ | 1 | 12 | — | SH |
| 13 | COOH | $-C(CH_3)_2$ | 1 | 1 | — | SH |
| 14 | (CH$_2$)$_2$—COOH | —C$_6$H$_5$ | 1 | 1 | — | H |
| 15 | (CH$_2$)$_2$—COOH | —C—C$_6$H$_5$ | 2 | 1 | — | H |

Starting Materials

NAC is commercially available from Aldrich Chemical Company, Milwaukee, Wis. in the United States and Europe. It is the acetyl amide of the amino acid cysteine. Its use has predominantly been as a mucolytic agent in the treatment of bronchial congestion and bronchitis. It chemically disrupts disulfide bonds in intra bronchial mucin, thus liquifying bronchial mucous plugs.

NAH was purchased from Fluka Chemical Company of Switzerland. N-Acetylcysteine ethyl ester is also commercially available.

N-DAC was synthesized in the following manner:

1-Cystine (0.05 mole, 12 g) was suspended in 50 ml of water and dissolved by adding 8 M potassium hydroxide until the solution was pH 12. At 0° C. to 3° C., acetic anhydride (0.15 mole 15.3 g) was added in small portions as the pH of the solution was maintained between 10 and 10.5 with 8 M potassium hydroxide. After the addition of acetic anhydride, the solution was allowed to stand one hour at room temperature at pH 10 and then adjusted to pH 3 with concentrated hydrochloric acid. The solution was concentrated in vacuo, and the viscous residue extracted three times with 100 ml portions of an acetone-water mixture (93:7 v/v). The acetone extract was concentrated in vacuo and dried in a desiccator over phosphorus pentoxide and sodium hydroxide. The residue was dissolved in ethanol. The precipitate that formed was removed by centrifugation and the remaining solution chromatographed on Silica Gel-G (Woelin). The columns were developed with chloroform:methanol:acetic acid (80:15:10 v/v). The columns were cut at $R_f=0.4$ and the N-DAC eluted with methanol. The methanol eluent was concentrated in vacuo to dryness over phosphorus pentoxide. The residue was dissolved in ethanol and the disulfide precipitated by adding the ethanolic solution to diethyl ether. The yield was 22%, and the melting point was 273-275. Anal. Calc. for $C_{10}H_{16}N_2S_2O_6$: C, 35.46; H, 5.20; N, 8.27%. Found: C, 35.94; H; 5.24; N, 8.17%.

General Synthesis Scheme for Substituted Cysteine Amides

To make the substituted cysteine amides shown in Examples 6, 7, and 8, the respective carbonyl chloride derived from p-nitrocinnamic (Example 6), p-nitrobenzoic (Example 7), or p-methoxycinnamic (Example 8)

acids (1 molar equivalents) were synthesized by refluxing the acids with four (4) times the molar equivalent of fresh thionyl chloride for 4.5 hours. The mixtures were concentrated, and the residues were dissolved in 20 weight volumes of dry pyridine and 10 volumes of dry methylene chloride or benzene. S-Benzylcysteine ethyl ester (3 molar equivalent) in 20 volumes of pyridine was added slowly to the above residue in pyridine. The reactions were maintained at less than 10 degrees centrigrade with external cooling for 4 fours, then stirred overnight.

The mixtures were partitioned with methylene chloride and 1 N sodium hydroxide. The organic phrase was washed with water until neutral and dried over sodium sulfate. The organic phrases were then dried under vacuum. The residues were recrystallized from ethanol water.

The nitro groups were reduced with sodium hydrosulfite (1:10 molar ratio nitro compound/sodium hydrosulfite) in stirring, refluxing aqueous acetone with excess 0.1 N sodium hydroxide (10 volumes). The solution was stirred for 30 minutes after the colors changed to yellow. Water was added (greater than 100 volumes) and the organic solvents removed under distillation. The aqueous solutions were neutralized with 10% acetic acid. The precipitates were recrystallized from ethanol.

The amines were methylated by the procedure of R. F. Borch and A. I. Hassid, *J. Org. Chem.* 37:1673-1674, 1972.

The protective benzyl groups were removed by stirring the respective S-benzyl derivatives in dry ether or tetrahydrofuran with freshly prepared, very dry Rainey nickel. The stirring continued at room temperature for 12 hours. The catalyst was removed by filtration and the solution evaporated to dryness. The residues were recrystallized from ethanol to yield the respective cysteine amides.

Topical Absorption in Man and Animals

There are no detectable blood levels of NAC, NAH, N-DAC, or NACE following the application of 5-20% concentrations of these agents in water three times a day to patients with open ulcers. In a rabbit animal model that was described previously (Cancer Treat. Rep. 65:1001, 1981), neither NAC, N-DAC nor NAH could be detected in the animal's circulation after topical application of 20% solution of the above agents to the surfaces of rabbit ears.

Method of Use

The following examples illustrate use of the invention.

EXAMPLE 16

In accordance with the present invention, wet gauze compresses of 20% N-DAC were applied four times a day to four patients with cutaneous ulcers resulting from herpes infections. In all cases, there was reduction in pain and inflammation within 48-72 hours. All lesions were cultured for baterial contamination, and when needed topical garamycin cream (0.1%) was applied twice daily along with the NAC solutions. All four patients demonstrated complete healing with minimal scarring and did not require additional therapy. Debridement of scar formation was performed as needed to allow the deep penetration of N-DAC.

One of these four cases was a 78 year old male who had herpes zoster ulcers over his left chest wall for seven days. The lesions were becoming worse with more drainage and pain. There were clusters of open ulcers with new vesicles developing each day. He was treated four times a day for thirty (30) minutes each time with wet gauze pads soaked with 20% N-DAC. The lesions became painless in 24 hours and all healed in two weeks. No recurrences were noted.

EXAMPLE 17

Six additional patients with herpes ulcers received topical applications of 20% NAC in water as soaked gauze pads applied to the lesions four to six times a day. All patients treated with NAC exhibited healing and did not require any additional treatment.

EXAMPLE 18

Two additional patients were treated with 20% NAH in a manner similar to that described in Example 17, with 100% healing.

One of these two patients was a 56 year old male who developed a herpes simplex genital ulcer on his penis. It was an isolated lesion, extremely painful and draining. He was treated topically with moist gauze pads of 20% N-DAC four times a day and the lesion was painless in 24 hours and healed in 10 days. No recurrence was noted in six months.

EXAMPLE 19

Four patients were treated who were suffering from cutaneous ulcers produced following accidental extravasation of DOX during intravenous administration of the drug. A 20% N-DAC (in water solution) was applied three times a day in the form of wet gauze compresses which remained in place. Within 48-72 hours in all cases there was areduction in pain, redness and inflammation. All lesions were cultured for bacterial contamination and where needed topical garamycin cream (0.1%) was applied twice daily along with the N-DAC solutions. All four patients demonstrated complete healing which did not require skin grafting. Debridement of scar formation was performed as needed to allow the deep penetration of N-DAC. A collagen scar was the result of the above applications of N-DAC.

One of these four patients was a 32-year old black female with advanced breast cancer who developed a painful skin ulcer following inadvertent DOX infiltration during her therapy. Accepted methods of treatment (intradermal sodium bicarbonate, dexamethasone, etc.) provided no relief, and she refused surgery. Gauze bandages soaked with N-DAC (20% solution) were applied four times a day over the ulcer. Over a 12-week period the lesion underwent scar formation and healed. After healing, the patient had complete leverage and rotation of the arm and wrist with complete scar formation.

EXAMPLE 20

Two patients with DOX-induced ulcers received topical applications of 20% NAC in water as continuous gauze soaks to the lesions. Both patients had permanent scar formation not requiring surgery following NAC application.

One of these patients was a 67-year old white female with advanced breast cancer which had spread to the lung and who was treated with DOX. During her therapy, a significant amount of DOX extravasated into her forearm. Over a one-month period a large ulcer formed, but she was not a candidate for general surgery to repair the lesion. She was treated with 20% NAC in water topically. The solution was applied three times a day to gauze pads over the lesion for two months. There was immediate reduction in pain and redness followed by continous scar formation with epithelialization and granulation until a permanent scar resulted that allowed free motion.

The effect of oral NAC on cardiac toxicities has been reported (U.S. Pat. No. 4,331,648) and shown not to reduce DOX antitumor activity. All six patients in Examples 19 and 20 were continued on chemotherapy—three continued on doxorubicin combinations and three on 5-Fluorourcil, Cyclophosphamide and Methotrexate therapy. No changes in response patterns were seen in the patients.

EXAMPLE 21

Psoriasis and radiation burns would be treated with N-DAC, NAC, NAH, NACE in the manner described in Examples 16-20.

EXAMPLE 22

Sunburn could be treated in the manner described in any of Examples 16-20. Alternatively, the compounds in any of Examples 5-8 could be topically applied to sunburned skin to promote healing and prevent additional sunburn damage.

Having illustrated and described the principles of my invention with reference to several preferred embodiments, it should be apparent to those persons skilled in the art that such invention may be modified in arrangement and detail without departing from such principles. I claim as my invention all such modifications as come within the true spirit and scope of the following claims.

I claim:

1. A compound for treating dermal inflammations, comprising:

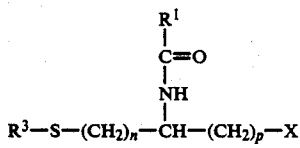

wherein $R^3$ is H or thiol; n is 1-12; p is 0-12; X is a substituted carbonyl; wherein

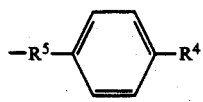

and wherein $R^4$ or $R^5$ is an electron donating group.

2. The compound of claim 1 wherein $R^4$ is a substituted or unsubstituted amine.
3. The compound of claim 1 wherein $R^5$ is an alkenyl.
4. The compound of claim 1 wherein $R^1$ is

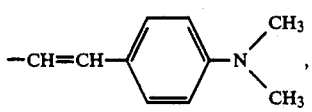

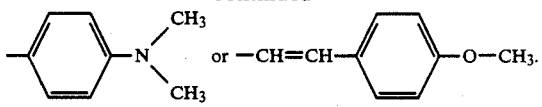

5. The compound of claim 1 wherein $R^3$ is

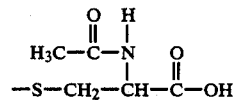

6. The compound of claim 1 wherein $R^3$ is H, n is 2, p is 0 and X is —COOH.
7. The compound of claim 1 wherein $R^3$ is H, n is 1, p is 0 and X is —COOH.
8. The compound of claim 1 wherein $R^3$ is H, n is 1, p is 0 and X is —COO—$CH_2$—$CH_3$.
9. The compound of claim 1 wherein the compound is

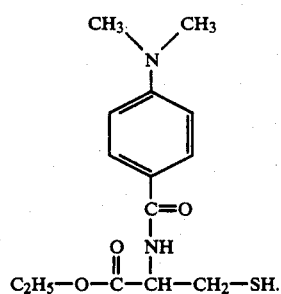

10. The compound of claim 1 wherein the compound is

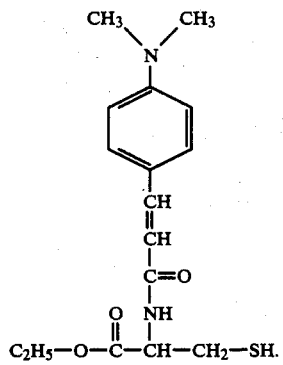

11. The compound of claim 1 wherein the compound is

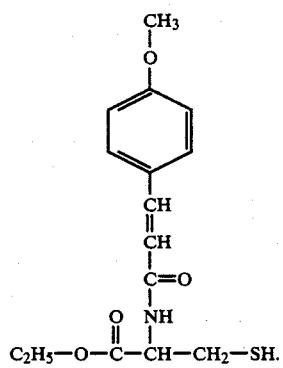

12. The compound of claim 1 wherein X is a carboxylic acid or ester.

UNITED STATES PATENT AND TRADEMARK OFFICE
CERTIFICATE OF CORRECTION

PATENT NO. : 4,827,016

DATED : May 2, 1989

INVENTOR(S) : Lee R. Morgan

It is certified that error appears in the above-identified patent and that said Letters Patent is hereby corrected as shown below:

In the Specification:

Column 11, line 10, "fours" should be --hours--.
Column 11, line 62, "baterial" should be --bacterial--.

In the Claims:

Column 13, line 50, "$R^1$ is" should be added after the word "wherein".

Signed and Sealed this

Fifth Day of June, 1990

Attest:

HARRY F. MANBECK, JR.

*Attesting Officer*  *Commissioner of Patents and Trademarks*